(12) United States Patent
Rosen

(10) Patent No.: US 8,242,048 B2
(45) Date of Patent: Aug. 14, 2012

(54) OXIDATION CATALYST AND ITS PREPARATION

(75) Inventor: Bruce I. Rosen, Park Ridge, IL (US)

(73) Assignee: BP Chemicals Limited, Middlesex (GB)

( * ) Notice: Subject to any disclaimer, the term of this patent is extended or adjusted under 35 U.S.C. 154(b) by 168 days.

(21) Appl. No.: 12/585,984

(22) Filed: Sep. 30, 2009

(65) Prior Publication Data

US 2011/0009666 A1    Jan. 13, 2011

Related U.S. Application Data

(62) Division of application No. 10/543,095, filed as application No. PCT/GB03/05399 on Dec. 11, 2003, now abandoned.

(60) Provisional application No. 60/442,527, filed on Jul. 27, 2003.

(51) Int. Cl.
*B01J 23/52* (2006.01)
*B01J 23/22* (2006.01)
*B01J 35/08* (2006.01)

(52) U.S. Cl. ............. 502/317; 502/8; 502/312; 502/313

(58) Field of Classification Search ........................ None
See application file for complete search history.

(56) References Cited

U.S. PATENT DOCUMENTS

| | | | |
|---|---|---|---|
| 2,435,379 A | 2/1948 | Archibald | 502/8 |
| 3,240,805 A | 3/1966 | Naglieri | |
| 6,130,356 A | 10/2000 | Karim et al. | |
| 6,333,444 B1 | 12/2001 | Ellis et al. | 585/658 |

FOREIGN PATENT DOCUMENTS

| | | |
|---|---|---|
| EP | 0 294 845 | 12/1988 |
| GB | 1 329 451 | 9/1973 |
| WO | WO 00/14047 | 3/2000 |

*Primary Examiner* — Paul A Zucker
(74) *Attorney, Agent, or Firm* — Nixon & Vanderhye

(57) ABSTRACT

Process for the selective oxidation of ethane to ethylene and/or acetic acid, and/or the selective oxidation of ethylene to acetic acid, by contacting ethane and/or ethylene with a molecular oxygen-containing gas at elevated temperature in the presence of a spray-dried supported catalyst composition. The supported catalyst composition includes molybdenum, vanadium and niobium metal components, supported on a support comprising alpha-alumina. The supported catalyst is prepared by forming a slurry of the metal components and alpha-alumina support particles or an alpha-alumina support precursor, and spray-drying the slurry.

29 Claims, 1 Drawing Sheet

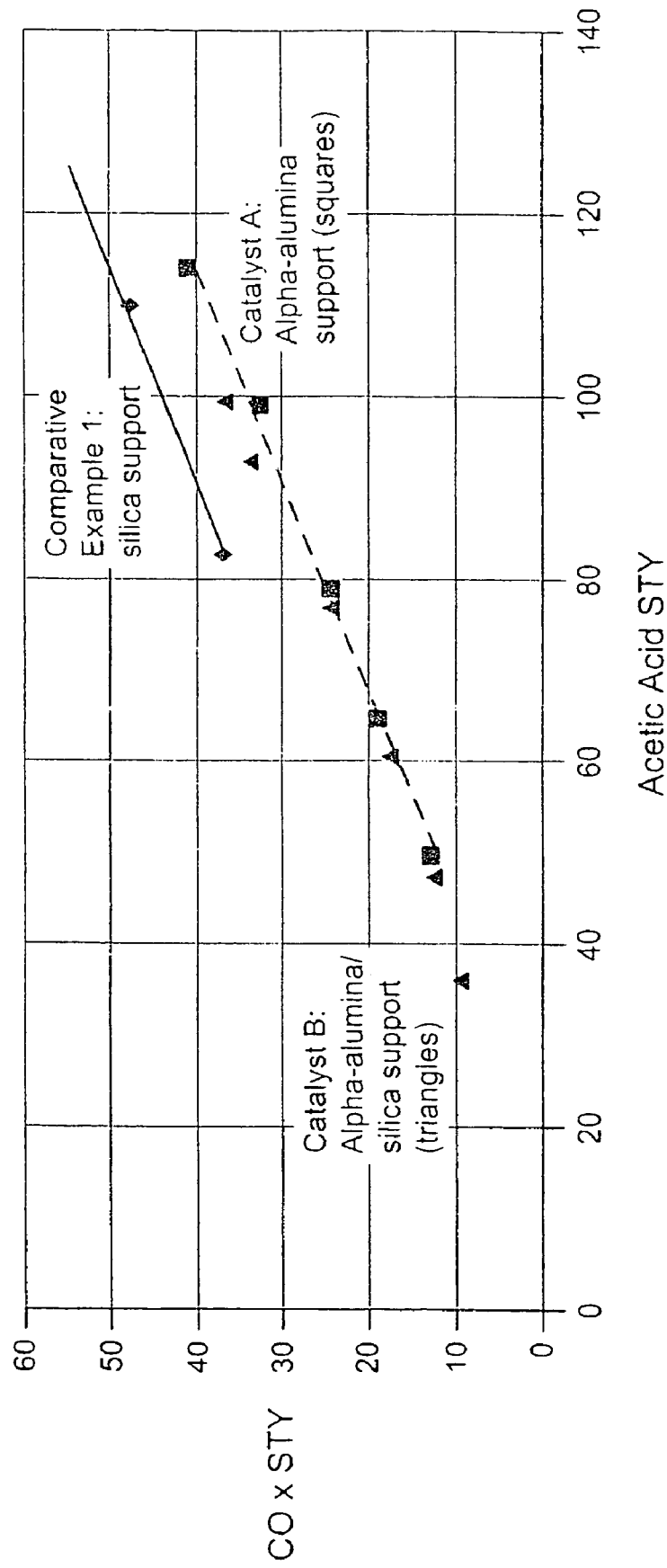

OXIDATION CATALYST AND ITS PREPARATION

This application is a divisional of application Ser. No. 10/543,095, filed Jul. 22, 2005, now abandoned, which is a 371 of PCT/GB2003/005399, filed Dec. 11, 2003, which claims priority to Provisional Application No. 60/442,527, filed Jan. 27, 2003, the entire content of which is hereby incorporated by reference in this application.

The present invention relates to a catalyst for the oxidation of ethane to ethylene and/or acetic acid and/or for the oxidation of ethylene to acetic acid, a method for preparation of said catalyst and to a process for the production of ethylene and/or acetic acid utilising the aforesaid catalyst.

Catalysts suitable for the oxidation of ethane to ethylene and/or acetic acid and/or for the oxidation of ethylene to acetic acid are well known. J. Catal. 52, 116-132 (1978), for example, discloses mixed oxide catalysts comprising molybdenum, vanadium and another transition metal, preferably niobium, for the oxidative dehydrogenation of ethane. The catalysts may be supported on alpha-alumina. The alumina-supported catalysts are prepared by impregnation followed by evaporation.

Further catalysts for use in the production of acetic acid by the oxidation of ethane and ethylene are known in the art from, for example, U.S. Pat. No. 4,250,346, EP-A-1043064, WO 99/20592, DE 196 30 832 and WO 00/14047.

U.S. Pat. No. 4,250,346 discloses the oxidative dehydrogenation of ethane to ethylene in a gas phase reaction at relatively high levels of conversion, selectivity and productivity to ethylene at a temperature of less than about 550° C. using as a catalyst a composition comprising the elements molybdenum, X and Y in the ratio MoaXbYc wherein X is Cr, Mn, Nb, Ta, Ti, V and/or W, and preferably Mn, Nb, V and/or W; Y is Bi, Ce, Co, Cu, Fe, K, Mg, Ni, P, Pb, Sb, Si, Sn, Tl and/or U, and preferably Sb, Ce and/or U, a is 1, b is 0.05 to 1.0 and c is 0 to 2, and preferably 0.05 to 1.0, with the proviso that the total value of c for Co, Ni and/or Fe is less than 0.5.

WO 99/20592 relates to a method of selectively producing acetic acid from ethane, ethylene or mixtures thereof and oxygen at high temperature in the presence of a catalyst having the formula $Mo_aPd_bX_cY_d$ wherein X represents one or several of Cr, Mn, Nb, Ta, Ti, V, Te and W; Y represents one or several of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and a=1, b=0.0001 to 0.01, c=0.4 to 1 and d=0.005 to 1.

German patent application DE 196 30 832 A1 relates to a similar catalyst composition in which a=1, b>0, c>0 and d=0 to 2. Preferably, a=1, b=0.0001 to 0.5, c=0.1 to 1.0 and d=0 to 1.0.

EP-A-1043064 discloses a catalyst composition for the oxidation of ethane to ethylene and/or acetic acid and/or for the oxidation of ethylene to acetic acid which comprises in combination with oxygen the elements molybdenum, vanadium, niobium and gold in the absence of palladium according to the empirical formula:

$$Mo_aW_bAu_cV_dNb_eY_f \qquad (1)$$

wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te and La; a, b, c, d, e and f represent the gram atom ratios of the elements such that: $0<a\leq 1$; $0\leq b<1$ and $a+b=1$; $10^{-5}<c\leq 0.02$; $0<d\leq 2$; $0<e\leq 1$; and $0\leq f\leq 2$.

WO 00/14047 discloses a process for the production of acetic acid which comprises contacting ethane and/or ethylene with a molecular oxygen containing gas in the presence of a microspheroidal fluidised particulate solid oxidation catalyst.

JP 61000447 A relates to a method of manufacturing a metal supported powder catalyst, said method comprising (1) providing a kneaded support raw material or a powder support, (2) suspending said support in a solution containing a suitable metal, (3) spray-drying the suspension and (4) calcining the dried material obtained. JP 61000447 A does not disclose catalysts suitable for oxidation of ethane to ethylene and/or acetic acid, and/or the oxidation of ethylene to acetic acid.

There remains a need to develop a catalyst for the oxidation of ethane to ethylene and/or acetic acid and/or for the oxidation of ethylene to acetic acid, and a process for the production of ethylene and/or acetic acid using said catalyst and wherein the catalyst enables a high selectivity to ethylene and/or acetic acid to be achieved.

Surprisingly, it has now been found that by using a catalyst on a support comprising alpha-alumina and which supported catalyst has been prepared by spray-drying, ethane may be oxidized to ethylene and/or acetic acid, and/or ethylene may be oxidized to acetic acid with increased selectivity to the desired products and with a reduced $CO_x$ formation.

Accordingly, in a first aspect, the present invention provides a method for the preparation of a supported catalyst composition suitable for the oxidation of ethane to ethylene and/or acetic acid, and/or the oxidation of ethylene to acetic acid, said supported catalyst composition comprising a catalyst comprising one or more metal components, supported on a support comprising alpha-alumina, which method comprises:

(a) forming a slurry of the one or more metal components and alpha-alumina support particles or an alpha-alumina support precursor; and
(b) spray-drying the slurry.

In a preferred embodiment, the method also comprises a further step (step (c)), wherein the spray-dried slurry is calcined.

The present invention also provides a supported catalyst composition suitable for the oxidation of ethane to ethylene and/or acetic acid, and/or the oxidation of ethylene to acetic acid, characterised in that the supported catalyst composition has been prepared according to the method of the first aspect of the invention.

The present invention requires a support comprising alpha-alumina. Preferably, the alpha-alumina may be pre-formed support particles. Suitably, the alpha-alumina used for the support has a surface area, as measured by BET, of less than 15 $m^2/g$, such as less than 10 $m^2/g$, for example, less than 5 $m^2/g$. Preferably the alpha-alumina has a surface area of at least 0.1 $m^2/g$, most preferably at least 0.5 $m^2/g$, such as in the range 0.5 $m^2/g$ to less than 10 $m^2/g$, more preferably in the range 0.5 $m^2/g$ to less than 5 $m^2/g$. The alpha-alumina preferably has a density of between 0.5 and 5 g/cc, preferably between 0.8 and 2 g/cc.

Commercially available alpha-alumina may be employed. Alternatively, pre-formed alpha-alumina can be formed from a suitable alpha-alumina precursor, for example, the alpha-alumina may be prepared by heating gamma-alumina or boehmite to a suitably high temperature (typically at least 500° C.) to effect a phase change to alpha-alumina.

The alpha-alumina employed in the present invention may be a combination of one or more alpha-aluminas. The support may be alpha-alumina or may comprise a mixture of alpha-alumina with one or more non-alpha-alumina materials, such as one or more other aluminas, for example gamma-alumina, or one or more non-aluminas, for example, silica or titania. Where one or more silicas are used in combination with one or more alpha-aluminas, the silicas are preferably low sodium-containing silicas.

Where the support comprises a mixture of alpha-alumina with one or more non-alpha-alumina materials; then the alpha-alumina should comprise at least 10% by weight of the total support. Preferably, the alpha-alumina comprises at least 20% by weight of the total weight of the support, more preferably 40% or more, and most preferably 50% or more.

The supported catalyst composition according to the present invention preferably has a surface area, as measured by BET, of between 0.1 and 20 $m^2/g$, more preferably between 1 and 5 $m^2/g$. The supported catalyst composition preferably has a density of between 0.5 and 5 g/cc, more preferably between 0.8 and 2 g/cc.

The one or more metal components are preferably present in the supported catalyst composition in a total amount equivalent to between 5% and 60% by weight of the total supported catalyst composition, preferably between 20 and 50% inclusive.

The supported catalyst composition is suitable for the oxidation of ethane to ethylene and/or acetic acid, and/or the oxidation of ethylene to acetic acid. Suitably, the catalyst comprises, as the one or more metal components, molybdenum, vanadium and niobium, in combination with oxygen. Suitable combinations of molybdenum, vanadium and niobium, for use in the present invention, are described in U.S. Pat. No. 4,250,346, EP-A-1043064, WO 99/20592 and DE 196 30 832, the contents of which are herein incorporated by reference.

In one embodiment of the present invention, the catalyst comprises, as a metal component, palladium. Suitable palladium containing catalysts are described, for example, in WO 99/20592, the contents of which are herein incorporated by reference. In particular, the catalyst of WO 99/20592 can be represented by the formula $Mo_aPd_bX_cY_d$ wherein X represents one or several of Cr, Mn, Nb, Ta, Ti, V, Te and W; Y represents one or several of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and a=1, b=0.0001 to 0.01, c=0.4 to 1 and d=0.005 to 1.

Preferably the catalyst comprises the metals molybdenum, vanadium, niobium and palladium.

In a second, and most preferred, embodiment of the present invention, the catalyst comprises the metals molybdenum, vanadium, niobium and gold in the absence of palladium according to the empirical formula:

$$Mo_aW_bAu_cV_dNb_eY_f \quad (1)$$

wherein Y is one or more metals selected from the group consisting of: Cr, Mn, Ta, Ti, B, Al, Ga, In, Pt, Zn, Cd, Bi, Ce, Co, Rh, Cu, Ag, Fe, Ru, Os, K, Rb, Cs, Mg, Ca, Sr, Ba, Zr, Hf, Ni, P, Pb, Sb, Si, Sn, Tl, U, Re, Te and La;
a, b, c, d, e and f represent the gram atom ratios of the metals such that:

$0 < a \leq 1; 0 \leq b < 1$ and $a+b=1$;

$10^{-5} \leq c \leq 0.02$;

$0 < d \leq 2$;

$0 < e \leq 1$; and $0 \leq f \leq 2$.

Catalysts embraced within the formula (I) include:

$$Mo_aW_bAu_cV_dNb_eY_f$$

$$Mo_aAu_cV_dNb_eY_f$$

$$Mo_aW_bAu_cV_dNb_e$$

$$Mo_aAu_cV_dNb_e$$

Examples of suitable catalysts having the formula (I) include: $Mo_{1.00}V_{0.25}Nb_{0.12}Au_{0.01}O_y$; $Mo_{1.00}V_{0.213}Nb_{0.138}Au_{0.007}O_y$; $Mo_{1.00}V_{0.232}Nb_{0.139}Au_{0.007}O_y$; $Mo_{1.000}V_{0.426}Nb_{0.115}Au_{0.0008}O_y$ and $Mo_{1.000}V_{0.529}Nb_{0.124}Au_{0.0012}O_y$, wherein y is a number that satisfies the valencies of the metals in the catalyst composition for oxygen.

Preferably a>0.01. Preferably, d>0.1. Preferably, e>0.01. Preferably, e≦0.5. Preferably, f≧0.01. Preferably, f≦0.5.

The catalyst according to this second embodiment may also comprise relatively high levels of niobium and vanadium, wherein the catalyst is as defined by formula (I) above, but with preferred ranges of d and e as follows: 0.4≦d≦0.865; 0.135≦e≦0.23; and 0.55≦d+e≦1.

Examples of suitable catalysts with these relatively high levels of Nb and V, and having the formula (I) include: $Mo_{1.00}V_{0.455}Nb_{0.200}Au_{0.0008}O_y$; $Mo_{1.00}V_{0.547}Nb_{0.163}Au_{0.0009}O_y$, and $Mo_{1.000}V_{0.661}Nb_{0.174}Au_{0.0009}O_y$, wherein y is a number which satisfies the valencies of the metals in the catalysts for oxygen.

For catalysts with these relatively high levels of niobium and vanadium, the preferred ranges of a, b, c, d, e, and f are as follows. Preferably, a>0.01, and most preferably a=1. Preferably, c>0.0001, and most preferably c>0.0005. Preferably, c≦0.002, and most preferably c≦0.001. Preferably, d≧0.425, such as d≧0.45, and, most preferably d≧0.5. Preferably, d≦0.8, and most preferably d≦0.7. Preferably, e≧0.14, and most preferably, e≧0.15. Preferably, e≦0.20, and most preferably e≦0.18. Preferably d+e≧0.6, such as d+e≧0.7. Most preferably d+e≧0.8. Preferably d+e≧0.95, more preferably d+e≦0.9. Preferably, f≦0.2, and most preferably f≦0.02.

Y, when present in any of the catalysts of this second embodiment, is preferably selected from the group consisting of Sn, Sb, Cu, Pt, Ag, Fe and Re.

The method of the present invention comprises forming a slurry of the one or more metal components, and alpha-alumina support particles or an alpha-alumina support precursor.

Preferably, the slurry is formed by mixing one or more solutions comprising the one or more metal components with alpha-alumina support particles or an alpha-alumina support precursor. The one or more solutions comprise soluble or insoluble compounds and/or complexes of the metal components of the catalyst. The prepared solution(s) are mixed with alpha-alumina or a suitable alpha-alumina precursor, and, if required, other support materials or suitable precursors to form the slurry.

Preferably, separate solutions comprising each metal component are prepared by dissolving sufficient quantities of soluble compounds and/or dispersing any insoluble compounds or quantities of said compounds so as to provide a desired gram-atom ratio of the metal components in the catalyst composition. Where the catalyst comprises more than one meta; component, the respective solutions are then mixed to form a single solution comprising the desired quantities of metal components.

The alpha-alumina support particles or alpha-alumina precursor (and, if required, other support materials or precursors) may then be added to the resulting solution.

Alternatively, the mixing of the solutions comprising each metal and the alpha-alumina support particles or alpha-alumina precursor (and, if required, other support materials or precursors) may be performed simultaneously.

The one or more solutions comprising the metal components may be prepared from any suitable metal compounds and/or complexes. The one or more solutions are preferably aqueous solutions having a pH in the range from 1 to 12, preferably from 2 to 8, at a temperature of from 20° to 100° C.

Suitable molybdenum-containing compounds, for example, include, molybdenum acetates, oxalates glycolates, oxides and halides. More preferably molybdenum may be introduced in the form of ammonium salts, such as ammonium heptamolybdate.

Suitable vanadium-containing compounds, for example, include, vanadium acetates, oxalates, tartrates, oxides and sulphates. More preferably vanadium may be introduced in the form of ammonium salts, such as ammonium metavanadate.

Suitable niobium-containing compounds, for example; include, niobium halides and oxalates. Preferably niobium may be introduced in the form of ammonium salts, such as ammonium niobium oxalate.

Suitable gold-containing compounds, for example, include, gold acetates and halides.

In the method of the present invention, the slurry of the one or more metal components and alpha-alumina support particles or an alpha-alumina support precursor, is spray-dried. Any suitable spray-drying techniques may be used. An overview of spray-drying can be found in a suitable handbook, such as, for example, K. Masters, Spray Drying Handbook, 1985, published by John Wiley and Sons.

In general, the outlet temperature of the spray-dryer should be high enough to ensure solvent removal, for example, at least 100° C. where water is used as the solvent, to ensure water removal. In addition, where the supported catalyst composition is to be calcined, it is preferred that the maximum inlet temperature of the spray-dryer used should not exceed the calcination temperature.

Suitably, spray-drying may be performed at an inlet temperature of between 250° C. and 350° C., for example, between 280° C. and 300° C. Suitable, the outlet temperature is between 120° C. and 180° C., for example, between 130° C. and 150° C.

Preferably, the spray-dried supported catalyst composition is calcined. Preferably calcination is performed by heating to a temperature of from 200 to 550° C., suitably in air or oxygen, and for a period of from 1 minute to 24 hours. The calcination procedure may also comprise subsequently heating the catalyst under nitrogen. The calcination may be performed in any suitable furnace, for example muffle furnace, or may be performed in situ in a reactor. Any calcination environment used, such as air or oxygen, may be slowly flowing during calcination.

Preferably, the spray-dried, optionally calcined, supported catalyst composition is in the form of spheroidal particles, more preferably microspheroidal particles. By the term "spheroidal particles", as used herein, is meant particles of essentially spherical shape. By the term "microspheroidal particles", as used herein, is meant particles of essentially spherical shape and of less than 300 microns diameter.

In another embodiment of the present invention there is provided a process for the selective oxidation of ethane to ethylene and/or acetic acid, and/or the selective oxidation of ethylene to acetic acid which oxidation process comprises contacting ethane and/or ethylene with a molecular oxygen-containing gas at elevated temperature in the presence of a spray-dried supported catalyst composition as hereinbefore described.

For use in the preparation of ethylene and/or acetic acid by the oxidation of ethane and/or ethylene, the supported catalyst composition has preferably been calcined, more preferably, by heating at a temperature in the range from 250 to 500° C. in the presence of an oxygen-containing gas, for example air.

The oxidation process may be carried out as a fixed bed process or as a fluidised bed process. However, the supported catalyst compositions of the present invention are especially suitable for the oxydehydrogenation of ethane in a fluidised bed. Hence, the oxidation process is preferably a fluidised bed process.

Where the supported catalyst composition is to be used in a fluidised bed oxidation process, the particle size is, preferably, such that at least 50% of the particles have a size less than 300 microns, most preferably such that at least 90% of the particle have a size of less than 300 microns. Preferably, the particles of supported catalyst composition for use in the fluidised bed oxidation process are microspheroidal particles.

For use in a fixed bed oxidation process, larger particles of the supported catalyst composition may be preferred, depending on the size of the fixed bed. Suitable particle sizes for a particular size of fixed bed may be readily calculated by the skilled man.

The desired size of the particles of the supported catalyst composition for use in the oxidation process may be achieved by use of pre-formed support particles of a suitable size in the preparation of the supported catalyst composition. The desired particle size may also be achieved from a wider range of particles sizes by the use of suitable sieves, optionally with grinding of larger particles.

Hence, where the supported catalyst composition is to be used in a fluidised bed oxidation process in the form of microspheroidal particles, this may be achieved by use of suitable pre-formed alpha-alumina granules of less than 300 microns size, preferably, pre-formed microspheroidal alpha-alumina, in the preparation of said supported catalyst composition.

Preferably, the supported catalyst composition for use in the oxidation process of the present invention comprises the metals molybdenum, vanadium, niobium and gold, in the absence of palladium, according to the empirical formula (I) as defined above. Most preferred supported catalyst compositions are as defined by the preferred values of a, b, c, d, e, f and Y as previously described.

The feed to the oxidation process of the present invention comprises ethane and/or ethylene, preferably ethane.

Ethane and/or ethylene may each be used in substantially pure form or admixed with one or more of nitrogen, methane, carbon dioxide and water in the form of steam, which may be present in major amounts, for example greater than 5 volume percent or one or more of hydrogen, carbon monoxide, $C_3/C_4$ alkenes and alkenes, which may be present in minor amounts, for example less than 5 volume percent.

The molecular oxygen-containing gas may be air or a gas richer or poorer in molecular oxygen than air, for example oxygen. A suitable gas may be, for example, oxygen diluted with a suitable diluent, for example nitrogen.

It is preferred to feed, in addition to ethane and/or ethylene and the molecular oxygen-containing gas, water (steam) because this can improve the selectivity to acetic acid.

Preferred feed compositions (in mol %) comprise, for example, 40 to 80% ethane, 0 to 10% ethylene, 0 to 20% water, 2 to 10% oxygen.

A balance of inert gas, preferably nitrogen, may be used.

The elevated temperature may suitably be in the range from 200 to 500° C. preferably from 200 to 400° C., and most preferably in the range of 260° C. to 360° C.

The pressure may suitably be atmospheric or superatmospheric, for example in the range from 1 to 50 bar, preferably from 1 to 30 bar.

The gas hourly space velocity (GHSV) may suitably be between 100 and 10,000 h$^{-1}$, preferably 1000 to 5000 h$^{-1}$.

Operating conditions and other information applicable to the oxidation process of the invention may be found in the aforesaid prior art, for example U.S. Pat. No. 4,250,346.

The present invention will now be further illustrated by reference to the following Examples and FIG. 1, wherein:

FIG. 1 shows a comparison of CO$_x$ Space-Time Yields (STY) for two catalysts according to the present invention compared to a spray-dried catalyst on silica.

CATALYST PREPARATION

Preparation of Mo, V, Nb, Au Slurry

The following three solutions were prepared:

Solution A: 427 g of ammonium heptamolybdate was dissolved in 550 g of water at 40-45° C. with stirring.

Solution B: 149 g of ammonium metavanadate was added to 1,500 g of water in a 2-liter beaker and heated to 73° C. The ammonium metavanadate did not completely dissolve.

Solution. C: 158 g of ammonium niobium oxalate was added to 600 g of water in a 6-liter stainless steel beaker and heated to 45° C. A sol formed within 30 minutes.

Solution C was added to solution B and allowed to digest at medium heat (defined as approximately 50-70° C.) for 30 minutes. Solution A was then added to the mixture, which was then stirred for 15 minutes at medium heat. 0.606 g AuCl$_3$ was then added to the entire slurry to give a slurry containing Mo, V, Nb and Au.

EXAMPLES ACCORDING TO THE PRESENT INVENTION

Catalyst A (Mo$_{1.000}$V$_{0.529}$Nb$_{0.124}$Au$_{0.0012}$O$_x$
(=Mo$_{60.5}$V$_{32}$Nb$_{7.5}$Au$^{0.07}$O$_x$)/spray-dried on alpha-alumina)

The slurry containing Mo, V, Nb and Au as prepared above was heated at a medium heat for at least 18 hours to reduce the volume of solution to a predetermined volume of about 70% of the original volume.

506 g of St Gobain SA 5396 alpha Al$_2$O$_3$ (Surface Area (SA) less than 1 m$^2$/g, density 1.27 g/cm$^3$) was then added to the stirred mixture. On the same day, the slurry was homogenized at 5,500 rpm for approximately 2 minutes. Spray drying was done in a mini-Niro spray-drier immediately after the solution was homogenized. Spray drying conditions were as follows: an inlet temperature of 290° C. inlet and an outlet temperature of 138° C.

The supported catalyst composition was calcined in air for 3 hours at 375° C. in a static muffle furnace before use.

The resulting spray-dried microspheroidal supported catalyst composition has a nominal composition Mo$_{60.5}$-V$_{32}$Nb$_{7.5}$Au$_{0.07}$O$_x$ on alpha-alumina, and at a nominal metal loading of 50% of the total catalyst weight. The supported catalyst composition had a surface area of 3 m$^2$/g and a density of 1.2 g/cm$^3$.

Catalyst B (Mo$_{1.000}$V$_{0.529}$Nb$_{0.124}$Au$_{0.0012}$O$_x$
(=Mo$_{60.5}$V$_{32}$Nb$_{7.5}$Au$_{0.07}$O$_x$/spray-dried on alpha-alumina/silica)

The slurry containing Mo, V, Nb and Au as prepared above was heated at a medium heat for at least 18 hours to reduce the volume of solution, as described above.

253 g of alpha Al$_2$O$_3$ and 858 grams of silica sol (Nalco TX11183, a low Na sol) was added to the stirred mixture. The mixture was further heated to reduce water volume to a level approximately equivalent to that after addition of the alumina in Example A. On the same day, the slurry was homogenized at 5,500 rpm for approximately 2 minutes. Spray drying was done in a mini-Niro spray-drier immediately after the solution was homogenized. Spray drying conditions were as follows: an inlet temperature of 290° C. inlet and an outlet temperature of 138° C.

The supported catalyst composition produced was calcined in air for 3 hours at 375° C. in a static muffle furnace before use.

The resulting spray-dried microspheroidal supported catalyst composition has a nominal composition Mo$_{60.5}$-V$_{32}$Nb$_{7.5}$Au$_{0.07}$O$_x$ on alpha-alumina/silica, and at a metal loading of 50% of the total catalyst weight, 25% alpha-alumina and 25% silica.

EXAMPLES NOT ACCORDING TO THE INVENTION

Comparative Example 1

(Mo$_{1.000}$V$_{0.529}$Nb$_{0.124}$Au$_{0.0012}$O$_x$
(=Mo$_{60.6}$V$_{32}$Nb$_{7.5}$Au$_{0.07}$O$_x$)/spray-dried on silica)

The slurry containing Mo, V, Nb and Au as prepared above was heated at a medium heat and stirred for at least 18 hours to reduce the volume of solution, as described above.

1,263 g of the silica sol (Nalco 2327), was then added to the stirred mixture and further heated to reduce water volume to a level approximately equivalent to that after addition of the alumina in Example A. The resulting slurry was homogenized at 5,500 rpm for approximately 2 minutes. Spray drying was done in a mini-Niro spray-drier immediately after the solution was homogenized. Spray drying conditions were as follows: an inlet temperature of 290° C. inlet and an outlet temperature of 138° C.

The supported catalyst composition was calcined in air for 3 hours at 375° C. C in a static muffle furnace before use.

The resulting spray-dried microspheroidal supported catalyst composition has a nominal composition Mo$_{60.5}$-V$_{32}$Nb$_{7.5}$Au$_{0.07}$O$_x$ on silica, at a nominal metal loading of 50% of the catalyst weight, and had a surface area of approximately 32 m$^2$/g.

Catalyst Testing Procedure

The catalyst to be used for testing was sieved to obtain a specific particle size distribution (psd) of 70% 230/325 mesh (50/50), 25% pans (fines) and 5% greater than 170 mesh.

The catalyst and an inert diluent (alpha alumina (SA 5396)) were added into a 40 cc fluidised bed reactor.

The reaction was performed at a temperature between 285° C. and 330° C. and at a reaction pressure of 16 bar. Ethane, ethylene (to mimic a recycle of ethylene), nitrogen and oxygen mixture was fed to the reactor using Brooks Mass Flow Controllers. Water was added by vaporisation and mixing with these feed gases prior to the reaction zone.

The volatile reactor effluent was sampled and analysed by gas liquid chromatography whereas water and acetic acid were condensed and analysed by gas liquid chromatography. The reactor bed temperature was monitored by a moving thermocouple:

The reaction conditions used with hours on stream (HOS) are given in Table 1.

TABLE 1

| | | Run Conditions (Feed mol %) | | | | | | |
|---|---|---|---|---|---|---|---|---|
| HOS | Max T °C. | Total Flow ml/min | GHSV h-1 | $C_2H_6$ | $C_2H_4$ | $H_2O$ | $O_2$ | $N_2$ |
| 1-21 | 288 | 471 | 3200 | 59.7 | 5.1 | 5.1 | 6.6 | 23.6 |
| 25-53 | 298 | 471 | 3200 | 59.7 | 5.1 | 5.1 | 6.6 | 23.6 |
| 56-73 | 310 | 471 | 3200 | 59.7 | 5.1 | 5.1 | 6.6 | 23.6 |
| 75-96 | 322 | 471 | 3200 | 59.7 | 5.1 | 5.1 | 6.6 | 23.6 |
| 97-116 | 336 | 471 | 3200 | 59.7 | 5.1 | 5.1 | 6.6 | 23.6 |

Pressure—16 bar

The results for Catalyst A under the above conditions are given in Table 2 (Sel.=selectivity, STY=Space-Time Yield, Conv.=Conversion):

As used herein, selectivity refers to a percentage that reflects the amount of desired acetic acid product produced as compared to the total carbon in the products formed:
% Selectivity=100*Moles of acetic acid produced/S wherein S=the molar acid-equivalent sum (carbon basis) of all carbon-containing products, excluding the alkane in the effluent.

TABLE 2

| HOS | Temp Max | Sel. $C_2H_4$ % | Ace-tic % | $CO_x$ % | STY $C_2H_4$ | Ace-tic | $CO_x$ | Conv. $C_2H_6$ % | $O_2$ % |
|---|---|---|---|---|---|---|---|---|---|
| 1-21 | 288 | 59 | 33 | 8 | 41 | 49 | 13 | 5 | 35 |
| 25-53 | 298 | 60 | 32 | 8 | 56 | 65 | 19 | 7 | 46 |
| 56-73 | 310 | 63 | 29 | 8 | 79 | 79 | 24 | 7 | 60 |
| 75-96 | 322 | 64 | 28 | 8 | 103 | 99 | 32 | 9 | 78 |
| 97-116 | 336 | 63 | 28 | 8 | 120 | 114 | 41 | 11 | 93 |

Comparison of the results from Catalyst A and Catalyst B, with Comparative Example 1, is shown in FIG. 1.

FIG. 1 shows that the supported catalyst compositions according to the present invention show a reduced $CO_x$ formation compared to a catalyst supported on silica alone. Selectivity to desired products (ethylene and acetic acid) is also higher for the supported catalyst composition of the present invention compared to the catalyst composition supported in silica.

The invention claimed is:

1. A process for the selective oxidation of ethane to ethylene and/or acetic acid, and/or the selective oxidation of ethylene to acetic acid, which oxidation process comprises contacting ethane and/or ethylene with a molecular oxygen-containing gas at elevated temperature in the presence of a spray-dried supported catalyst composition said supported catalyst composition comprising a catalyst comprising molybdenum, vanadium and niobium metal components, supported on a support comprising alpha-alumina, which supported catalyst is prepared by a method comprising:
   (a) forming a slurry of the metal components and alpha-alumina support particles or an alpha-alumina support precursor; and
   (b) spray-drying the slurry.

2. The process according to claim 1, wherein the supported catalyst composition is calcined.

3. The process according to claim 1, wherein the alpha-alumina used for the support has a surface area, as measured by BET, of less than 15 m²/g.

4. The process according to claim 1, wherein the alpha-alumina used for the support has a surface area, as measured by BET, of at least 0.1 m²/g.

5. The process according to claim 1, wherein the alpha-alumina used for the support has a density of between 0.5 and 5 g/cc.

6. The process according to claim 1, wherein the support is alpha-alumina.

7. The process according to claim 1, wherein the support comprises a mixture of alpha-alumina with one or more non-alpha-alumina materials.

8. The process according to claim 7, wherein the support comprises one or more alpha-aluminas in combination with one or more silicas and wherein the one or more silicas are low sodium-containing silicas.

9. The process according to claim 7, wherein alpha-alumina comprises at least 10% by weight of the total support.

10. The process according to claim 1, wherein the supported catalyst composition has a surface area, as measured by BET, of between 0.1 and 20 m²/g.

11. The process according to claim 1, wherein the supported catalyst composition has a density of between 0.5 and 5 g/cc.

12. The process according to claim 1, wherein the one or more metal components are present in the supported catalyst composition in a total amount equivalent to between 5% and 60% by weight of the total supported catalyst composition.

13. The process according to claim 1, wherein the catalyst further comprises gold in the absence of palladium according to the empirical formula:

$$Mo_aW_bAu_cV_dNb_eY_f \quad (I)$$

wherein Y is one or more metals selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te and La; a, b, c, d, e and f represent the gram atom ratios of the metals such that:
   $0<a\leq1$; $0\leq b<1$ and $a+b=1$;
   $10^{-5}<c\leq0.02$;
   $0<d\leq2$;
   $0<e\leq1$; and
   $0\leq f\leq2$.

14. The process according to claim 2, wherein the supported catalyst composition has been calcined by heating at a temperature in the range from 250 to 500° C. in the presence of an oxygen-containing gas.

15. The process according to claim 1, which is a fluidised bed process.

16. The process according to claim 1, wherein the particle size of the supported catalyst composition is such that at least 50% of the particles have a size less than 300 microns.

17. The process according to claim 16, wherein the supported catalyst composition is in the form of microspheroidal particles.

18. The process according to claim 1, wherein there is fed, in addition to ethane and/or ethylene and the molecular oxygen-containing gas, water (steam).

19. The process according to claim 1, wherein there is fed to the process a feed composition (in mol %) comprising 40 to 80% ethane, 0 to 10% ethylene, 0 to 20% water, 2 to 10% oxygen and with a balance of inert gas.

20. The process according to claim 1, wherein the elevated temperature is in the range from 200 to 500° C.

21. The process according to claim 1, wherein the process is operated at a pressure in the range from 1 to 50 bar.

22. The process according to claim 1, wherein the process is operated with a gas hourly space velocity (GHSV) of between 100 and 10,000 h⁻¹.

23. The process according to claim 1, wherein the oxygen-containing gas is air.

24. The process according to claim 1, wherein the particle size of the supported catalyst composition is such that at least 90% of the particles have a size of less than 300 microns.

25. The process according to claim 1, wherein the inert gas is nitrogen.

26. The process according to claim 1, wherein the elevated temperature is in the range from 200 to 400° C.

27. The process according to claim 1, wherein the elevated temperature is in the range from 260° C. to 360° C.

28. The process according to claim 1, wherein the process is operated at a pressure in the range from 1 to 30 bar.

29. The process according to claim 1, wherein the process is operated with a gas hourly space velocity (GHSV) of between 1000 to 5000 $h^{-1}$.

* * * * *